United States Patent
Deichmann et al.

(10) Patent No.: US 10,203,320 B2
(45) Date of Patent: Feb. 12, 2019

(54) LABEL FREE METHOD FOR ASSESSING CHEMICAL CARDIOTOXICITY

(71) Applicant: Corning Incorporated, Corning, NY (US)

(72) Inventors: Oberon Denaci Deichmann, Corning, NY (US); Ye Fang, Painted Post, NY (US); Ann MeeJin Ferrie, Painted Post, NY (US); David Henry, Fontaine le Port (FR); Haibei Hu, Glen Allen, VA (US); Corinne Walerack, Veneux les sablons (FR); Qi Wu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 570 days.

(21) Appl. No.: 14/437,275

(22) PCT Filed: Nov. 15, 2013

(86) PCT No.: PCT/US2013/070281
§ 371 (c)(1),
(2) Date: Apr. 21, 2015

(87) PCT Pub. No.: WO2014/078646
PCT Pub. Date: May 22, 2014

(65) Prior Publication Data
US 2015/0268222 A1   Sep. 24, 2015

Related U.S. Application Data

(60) Provisional application No. 61/726,620, filed on Nov. 15, 2012.

(51) Int. Cl.
| | | |
|---|---|---|
| *G01N 33/50* | (2006.01) | |
| *G01N 15/14* | (2006.01) | |
| *G01N 21/31* | (2006.01) | |
| *G01N 21/77* | (2006.01) | |
| *G01N 15/00* | (2006.01) | |

(52) U.S. Cl.
CPC ..... *G01N 33/5014* (2013.01); *G01N 15/1429* (2013.01); *G01N 15/1434* (2013.01); *G01N 15/1456* (2013.01); *G01N 15/1463* (2013.01); *G01N 21/3151* (2013.01); *G01N 21/7743* (2013.01); *G01N 33/5061* (2013.01); *G01N 33/502* (2013.01); *G01N 2015/0065* (2013.01); *G01N 2015/144* (2013.01); *G01N 2015/1454* (2013.01)

(58) Field of Classification Search
None
See application file for complete search history.

(56) References Cited

U.S. PATENT DOCUMENTS

| | | |
|---|---|---|
| 7,960,170 B2 | 6/2011 | Schulz et al. |
| 8,076,090 B2 | 12/2011 | Fang et al. |
| 8,703,428 B2 | 4/2014 | Fang et al. |
| 8,846,575 B2 | 9/2014 | Fang et al. |
| 9,222,000 B2 | 12/2015 | Frutos et al. |
| 2008/0220516 A1 | 9/2008 | Eddington et al. |
| 2009/0054954 A1 | 2/2009 | Foley et al. |
| 2009/0099038 A1 | 4/2009 | Deisseroth et al. |
| 2009/0257990 A1 | 10/2009 | Feld et al. |
| 2010/0129854 A1 | 5/2010 | Fang et al. |
| 2010/0143959 A1 | 6/2010 | Cunningham et al. |
| 2010/0190229 A1 | 7/2010 | Zhang et al. |
| 2011/0039294 A1 | 2/2011 | Wang et al. |
| 2011/0300569 A1 | 12/2011 | Li et al. |

FOREIGN PATENT DOCUMENTS

| | | |
|---|---|---|
| WO | 2004057333 A1 | 7/2004 |
| WO | 2009025819 A1 | 2/2009 |
| WO | 2009062107 A1 | 5/2009 |
| WO | 2011116260 | 9/2011 |
| WO | 2012009602 | 1/2012 |

OTHER PUBLICATIONS

Ferrie et al., "High resolution resonant waveguide grating imager for cell cluster analysis under physiological condition", Applied Physics Letters, 100, 223701-1-223701-4, (2012).
International Search Report, issued in connection with corresponding PCT application No. PCT/US2013/070281, dated Nov. 15, 2013.
English Translation of First Office Action in Corresponding CN Patent Application No. 201380070133.X, dated June 1, 2017, China Patent Office, 7 pages.
Fang Y. et al., "Label-free cell-based assays for GPCR screening." Combinatorial Chemistry & High Throughput Screening, vol. 11, No. 5, pp. 357-369, Jun. 2008.
Fang Y., "Label-Free Cell-Based Assays with Optical Biosensors in Drug Discovery." ASSAY and Dug Development Technologies, vol. 4, No. 5, pp. 583-595, Oct. 2006.
Fang Y., "Non-Invasive Optical Biosensor for Probing Cell Signaling." Sensors, vol. 7, pp. 2316-2329, Oct. 16, 2007.
Ferrie, A. et al., "Resonant waveguide grating imager for live cell sensing." Applied Physics Lettets, vol. 97, pp. 223704-1 to 223704-3, Dec. 10, 2010.

*Primary Examiner* — Kaijiang Zhang
(74) *Attorney, Agent, or Firm* — John P. Ciccarelli

(57) ABSTRACT

A label-free resonant waveguide grating biosensor imager system for measuring beat patterns and dynamic mass redistribution (DMR) signals of cultured cardiomyocytes in the absence and presence of a drug molecule. The disclosure also provides a method using the imager system for analyzing the beat patterns and the DMR signals of the cardiomyocytes to assess drug-induced cardiotoxicity.

12 Claims, 7 Drawing Sheets

LABEL FREE METHOD FOR ASSESSING CHEMICAL CARDIOTOXICITY

CROSS-REFERENCE TO COPENDING U.S. APPLICATION

This application is related to commonly owned and assigned U.S. Provisional Application Ser. No. 61/117,838, filed on Nov. 25, 2008, and Ser. No. 12/613,966, filed on Nov. 11, 2008, entitled "Liver Cell Toxicity Assay", now U.S. Patent Publication No. 20100129854, but does not claim priority thereto. The content of this document and the entire disclosure of any publications or patent documents mentioned herein are incorporated by reference. This application claims the benefit of priority to U.S. Application No. 61/726,620 filed Nov. 15, 2012, the content of which is incorporated hereby reference in its entirety.

FIELD

The disclosure is related to a label-free resonant waveguide grating (RWG) biosensor apparatus and methods to assess, for example, cardiac biology or drug-induced cardiotoxicity.

BACKGROUND

Drug-induced adverse effects in human and animals are known and have been largely associated with the malfunctioning of major organs such as heart, liver, and kidney. The potential for adverse drug effects adds a level of complexity to safe therapeutic application. Along with hepatotoxicity, assessment of cardiotoxicity is a significant component of drug discovery and the drug development process. Drug-induced cardiotoxicity is an adverse event associated with certain drugs including some chemotherapeutic agents used to treat hematologic and solid malignancies, and often leads to morbidity and high mortality. Numerous biochemical, cellular and tissue studies in the past decades have suggested that drug-induced cardiac abnormality is associated with the changes in the activity of, for example, ion channels, myocyte structure, extracellular matrix (ECM) structure, and neurohumoral system. Drug cardiotoxicity can also results in protein abnormalities related to $Ca^{2+}$ and abnormalities of the signaling system. Among these factors, the change in ion channel activity has been recognized as a major cause of drug-induced cardiotoxicity. Numerous overlapping ionic currents contribute to regulate the morphology and duration of ventricular action potential duration. Depolarization of the ventricles is initiated by the rapid entry of $Na^+$ through selective sodium channels. This is followed by a rapid repolarization through transiently activating and inactivating outward potassium channels, and subsequently by a plateau phase, mainly determined by the entry of calcium ions through L-type calcium channels. During repolarization the negative transmembrane potential is recovered by the inactivation of calcium channels and the increase in net outward potassium currents carried mainly by the slow and rapid components of the delayed rectifier potassium channels. Inwardly-rectifying potassium channels also contribute to the repolarization. The regulatory factors including $Na^+/K^+$-pump restore intracellular ion concentrations to the original state.

Assessment of drug cardiotoxicity is significant for the safe development of novel pharmaceuticals. Assessing a compound's risk for prolongation of the surface electrocardiographic QT interval and hence risk for life-threatening arrhythmias is an FDA (US Food and Drug Administration) mandate before approval of nearly all new pharmaceuticals in the US. The QT interval is a measure of the time between the start of the Q wave and the end of the T wave in the heart's electrical cycle. In general, the QT interval represents electrical depolarization and repolarization of the left and right ventricles. A lengthened QT interval is a biomarker for ventricular tachyarrhythmias, such as torsades de pointes (TdP), and a risk factor for sudden death. QT prolongation has most commonly been associated with loss of current through hERG (human ether-a-go-go related gene) potassium ion channels due to a direct block of the ion channel by drugs or occasionally by inhibition of the plasma membrane expression of the channel protein. In the majority of cases, drugs that prolong the QT interval preferentially inhibit the rapid component of the delayed rectifier potassium current channel (I(Kr)), or hERG, the gene that encodes for the alpha-subunit of IKr channels.

A widely recognized in vivo drug cardiotoxicity assessment method is the electrocardiogram (ECG) test. The surface ECG provides information on the electrical events including atrial/ventricular depolarization and ventricular repolarization within the heart. In ECG, the QT interval indicates ventricular depolarization (i.e., a decrease in the electrical potential across a membrane) and repolarization (i.e., recovery of the resting potential). The ECG represents the duration of the ventricular action potential and includes the QT interval, which interval reflects activation time of both ventricles. Although most drug-induced QT prolongation is associated with the inhibition of hERG, the opposing correlate that inhibition of the hERG channel causes a long QT interval has not been conclusively proven. In addition, cardiotoxicity can also be generated by changes in ion pump activities and by cardiomyocyte cell death. Early identification of adverse drug-induced risk can be beneficial in assessing multiple ion channels at a molecular level, cell proliferation, and cell death. Cardiotoxicity testing has become a central component of drug development.

There are several other techniques used for in vitro evaluation of drug-induced cardiotoxicity, including the patch clamp technique using hERG transfected cells or isolated cardiomyocytes, $Rb^+$ efflux assay, microelectrode assay using Purkinje fibers or guinea pig papillary muscle, and bioimpedance based cardiomyocyte profiling. Among them, the patch clamp technique is probably the most widely used tool for screening of drug-induced cardiotoxicity that allows monitoring the effect of only a single drug on a single target ion channel at a time. Although this technique provides high accuracy, it does not allow for contemporaneous observation of multiple ion channel activities, and does not allow for systematic presentation of drug cardiotoxicity including cell death and alterations in cell signaling. Most of the other available technologies are associated with the averaged measurement of a population of cells. A label-free whole cell assay method that can integrate single cell biology with population behavior of cardiovascular cells would be highly advantageous.

SUMMARY

The disclosure provides a high frequency label-free resonant waveguide grating (RWG) biosensor imager system and method for measuring the beat pattern and the dynamic mass redistribution (DMR) of cultured cardiomyocytes in the absence and presence of a chemical substance, such as a drug molecule. The label-free apparatus and method use a high frequency swept wavelength interrogation of a resonant waveguide grating biosensor to detect the beating pattern of the cultured cardiomyocytes. In embodiments, the disclosure also provides a data analysis method to assess the potential of drug-induced cardiotoxicity.

BRIEF DESCRIPTION OF DRAWINGS

In embodiments.

DETAILED DESCRIPTION

Figure 1:
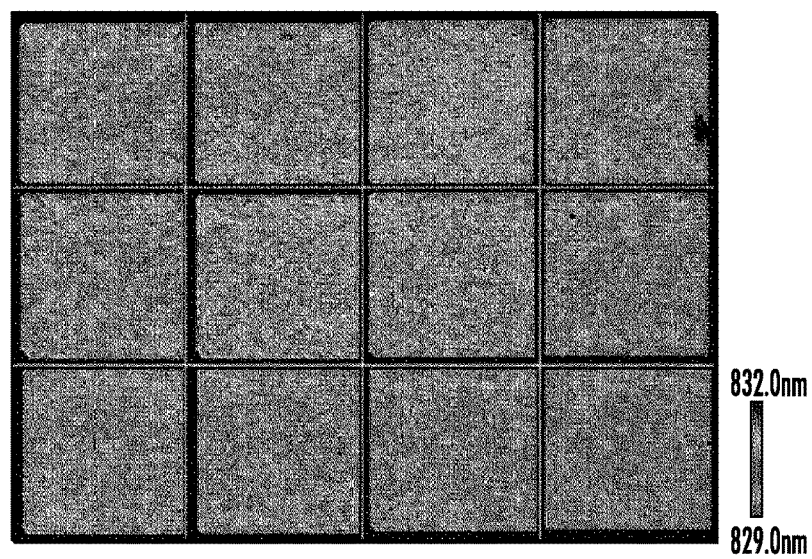
FIG. 1 shows a false colored high resolution resonant wavelength image of a 3×4 array of resonant waveguide grating biosensors in an EPIC® 384 well microplate having cultured human iPS-derived cardiomyocyte cells.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed apparatus, and the disclosed method of making and using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

The "central resonant wavelength" refers to the wavelength that provides the maximum coupling efficiency of the illuminating light into the waveguide grating biosensor.

"Include," "includes," or like terms means encompassing but not limited to, that is, inclusive and not exclusive.

"About" modifying, for example, the quantity of an ingredient in a composition, concentrations, structural dimensions, volumes, process temperature, process time, yields, flow rates, pressures, viscosities, and like values, and ranges thereof, employed in describing the embodiments of the disclosure, refers to variation in the numerical quantity that can occur, for example: through typical measuring and handling procedures used for preparing materials, compositions, composites, concentrates, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for structure, components, ingredients, additives, and like aspects, and ranges thereof, are for illustration only; they do not exclude other defined values or other values within defined ranges. The methods of the disclosure can include any value or any combination of the values, specific values, more specific values, and preferred values, including intermediate values and ranges.

In vitro culturing of cells provides material useful for research in pharmacology, physiology, and toxicology. Recent advances in pharmaceutical screening techniques allow pharmaceutical companies to rapidly screen vast libraries of compounds against therapeutic targets.

Cardiotoxicity is a condition that can result in damage to the heart muscle. Drug-induced cardiotoxicity refers to cardiotoxicity that affects the heart by drugs, and includes the direct effect of the drug on the heart but can also include the indirect effect, for example, due to enhancement of haemodynamic flow alterations or due to thrombotic events. Cardiotoxicity, if severe, can lead to cardiomyopathy. Cardiomyopathy is often a result of treatments, such as chemotherapeutic medications, or can be caused by a group of diseases or disorders, that lead to damaged heart muscle. Injury to heart muscle may cause a disturbance in the heart's pumping action, and subsequent heart failure.

Drug-induced cardiotoxicity commonly results in left ventricle dysfunction, rhythm disturbances, and ischemia. These toxic effects can range from subclinical abnormalities to life-threatening states. The effects may be related to drug exposure or medical therapy, but also to long term cardiovascular effects. Medications that can commonly cause cardiotoxicity, or cardiomyopathy, include, for example, anthracyclines. Anthracyclines including doxorubicin can be used to treat leukemia, lymphoma, multiple myeloma, breast cancer, sarcoma, and other cancers. The anthracycline-associated cardiotoxicity (AAC) has been long recognized, and can be divided into three forms: immediate pericarditis-myocarditis syndrome, an early-onset chronic progressive form, and a late-onset chronic progressive form. The main hypothesis for the underlying mechanism of AAC is the generation of reactive free radical species that interact and damage cellular membranes. Other possible mechanisms can include, for example, the induction of apoptosis, mitochondrial DNA damage, changes in ATP production, and down regulation of mRNA expression for sarcoplasmic reticulum calcium ATPase.

The development of new drugs in the past decades has revealed a new spectrum of pro-arrythmogenic effects of drugs, particularly anticancer drugs, and the most important one resulting in QT interval prolongation. The definition of QTc prolongation varies in the literature, but most regard normal QTc as less than or equal to 400 milliseconds (ms), and prolonged QTc as greater than 450 ms in men and greater than 470 ms in women. Ventricular arrhythmias, particularly torsades des pointes are correlated with QTc greater than or equal to 550 ms, but there is no threshold below which prolongation QT interval is considered free of pro-arrhythmic risk. A widely accepted hypothesis about the aetiology of QT prolongation is an interaction with HERG K channels. HERG K channels allow the rapid component of myocardial repolarization; when a drug interferes with their function, the potassium inflow decreases leading to prolongation of repolarization. Cancer patients can be prone to QT prolongation as many of them have electrolyte disturbances, take concomitant medications that could enlarge QT interval such as antiemetics, antifungals or antibiotics, or have baseline electrocardiogram abnormalities (up to 32% of patients).

Sudden unexpected deaths from heart arrest have been reported with use of non-cardiac drugs since the early 1960s. These drugs, which cause sudden death, have centered on torsade de pointes (TdP), a polymorphic ventricular arrhythmia that can progress to ventricular fibrillation and sudden death. Prolongation of the QTc interval is a surrogate marker for the ability of a drug to cause TdP. Arrhythmias are more likely to occur if drug-induced QTc prolongation coexists with other risk factors, such as individual susceptibility, presence of congenital long QT syndromes, heart failure, bradycardia, electrolyte imbalance, overdose of a QTc-prolonging drug, female sex, restraint, old age, hepatic or renal impairment, and slow metabolic status. Pharmacodynamic and pharmaco-kinetic interactions can also increase the risk of arrhythmias.

Pharmacology safety concern is the major cause of drug attrition during the clinical development phases and account for approximately 35 to 40% of all drug attrition. Of these, cardiovascular related toxicities dominate, with 19% of the withdrawn drugs. A significant proportion of these toxicities is due to functional and dose dependent effects. Approximately half of the 19% withdrawals are caused by arrhythmia effects, including potentially life threatening states such as drug induced torsades de pointes (TdP). Furthermore, concern about a relationship between QTc prolongation, TdP, and sudden death applies to a wide range of drugs. Several cardiac and non-cardiac drugs have been withdrawn from the market due to cardiovascular toxic effects in humans. Although no toxic effects were observed in animals, the pharmaceutical regulatory authorities have extended cardiotoxicity testing requirements.

In embodiments, the disclosure provides a label-free method to detect a drug-induced cardiac effect comprising:

culturing a cardiomyocyte cell on the surface of at least one resonant waveguide grating (RWG) biosensor;

illuminating the at least one RWG biosensor using a swept wavelength interrogation resonant waveguide grating biosensor imager with a first light source having a first wavelength;

collecting the resonant spectra at all pixelated locations of the at least one biosensor and determining the average of the central resonant wavelengths of all pixelated locations of the at least one RWG biosensor with the swept wavelength interrogation resonant waveguide grating biosensor imager;

illuminating the at least one RWG biosensor using a second light source having a second wavelength;

monitoring with the imager, in real time, the intensity of the resonantly reflected light from the at least one RWG biosensor by illuminating with the second light source to obtain a beating spectrum of the cardiomyocyte cell in a resting state;

contacting the resting state cardiomyocyte cell with a drug molecule;

illuminating of the drug-contacted cardiomyocyte cell on the surface of the at least one RWG biosensor using the second light source;

monitoring with the imager, in real time, the intensity of the resonantly reflected light from the at least one RWG biosensor by illuminating with the second light source to obtain a beating spectrum of the drug-contacted cardiomyocyte cell; and extracting and comparing the at least one beating parameter of the beating spectrum of the resting state cardiomyocyte cell and the beating spectrum of the drug-contacted cardiomyocyte cell, wherein the drug-induced alteration of the at least one beating parameter is an indicator of the cardiac effect of the drug.

In embodiments, the cardiomyocyte cell is a human primary cardiomyocyte, an animal primary cardiomyocyte, a human embryonic stem cell derived cardiomyocyte, a human induced pluripotent stem cell (iPS cell) derived cardiomyocyte, and an animal induced pluripotent stem cell (iPS cell) derived cardiomyocyte, and a combination thereof.

In embodiments, the surface of the resonant waveguide grating biosensor contains a coating with an extracellular matrix protein, or a cardiomyocyte compatible synthetic material. The extracellular matrix protein can be, for example, fibronectin, matrigel, collagen I, collagen IV, and gelatin, and the combination thereof. The cardiomyocyte compatible synthetic material can be, for example, poly (HEMA-co-MAA-PEO4-vitronectin) peptide conjugate.

In embodiments, the resonant waveguide grating biosensor imager can be, for example, a swept wavelength interrogation imaging system. In embodiments, the biosensor imager can have, for example, a spatial resolution from 3 microns to 500 microns, for example, 3 microns, 6 microns, 12 microns, 25 microns, 50 microns, 100 microns, or 500 microns, including intermediate values and ranges. In a preferred embodiment, the biosensor imager can have a spatial resolution of 12 microns. In embodiments, the resonant waveguide grating biosensor imager can be, for example, an optical fiber based wavelength interrogation resonant wavelength grating biosensor system, wherein the system can be used to scan the biosensor.

In embodiments, the resonant waveguide grating biosensor can include an array of biosensors. In a preferred embodiment, the biosensor array can be, for example, a Society for Biomolecular Screening-compatible microtiter plate.

In embodiments, the wavelength of the second light source can be, for example, from 100 picometers to 1,500 picometers (pm) above the average of the central resonant wavelengths of all pixelated locations of the at least one RWG biosensor, for example, 100 pm, 200 pm, 300 pm, 400 pm, 500 pm, 600 pm, 800 pm, 1000 pm, or 1500 pm, including intermediate values and ranges.

In embodiments, the wavelength of the second light source is from 100 picometers to 1,500 picometers (pm) below the average of the central resonant wavelengths of all pixelated locations of the at least one RWG biosensor, for example, 100 pm, 200 pm, 300 pm, 400 pm, 500 pm, 600 pm, 800 pm, 1000 pm, or 1500 pm, including intermediate values and ranges.

In embodiments, the illuminating light can have a wavelength that is the averaged wavelength of the central resonant wavelengths of all pixelated locations of the at least one RWG biosensor. The central resonant wavelength is the wavelength that provides the maximum coupling efficiency of the illuminating light into the waveguide grating biosensor. When the illuminating light has a wavelength that is higher than the average of the central resonant wavelength of the biosensor, the resultant beating spectrum of the cardiomyocyte cells consists of a series of minimal valleys arising from the beating of the cells. Conversely, when the illuminating light has a wavelength that is lower than the average of the central resonant wavelength of the biosensor, the resultant beating spectrum of the cardiomyocytes consists of a series of maximum peaks arising from the beating of the cell. When the illuminating light has a wavelength that is the same the average of the central resonant wavelength of the biosensor, the resultant beating spectrum of the cardiomyocytes consists of a series of peaks and valleys arising from the beating of the cell depending on the basal resonant wavelength pixelated position of the biosensor, due to the wide distribution of the basal resonant wavelength at different pixelated positions of the biosensor.

In embodiment, culturing the cardiomyocyte cell can be performed for a long period of time until synchronized beating of most cardiomyocyte cells within a biosensor has been reached. The culturing time depends on the type of cardiomyocyte cells, but typically ranging from 5 days to 2 weeks. In embodiments, culturing the cardiomyocyte cell can be performed in a short period of time, typically less than 1 week, so that only spontaneous beating has occurred.

In embodiments, the drug molecule can be, for example, a marketed drug molecule, a pre-clinically used drug candidate molecule, a test drug molecule, or a combination thereof.

In embodiments, the cardiomyocyte cell beating spectrum can have a temporal resolution of from 0.01 second to 1 second, for example, 0.01 sec, 0.05 second, 0.1 second, 0.2 second, 0.5 second, 1 second, including intermediate values and ranges.

In embodiments, the cardiomyocyte cell beating spectrum can be obtained, for example, in from about 1 minute to 5 days after exposure to the drug molecule, for example, from 1 min, 15 min, 30 min, 60 min, 240 min, 8 hours, 12 hours, 16 hours, 1 day, 2 days, 4 days, and 5 days, including intermediate values and ranges, after the treatment with the drug molecule. The beating spectra of the cultured cardiomyocyte cells obtained at different time points after the drug treatment can be used to classify the toxicity of the drug molecules.

In embodiments, the at least one beating parameter of the beating spectrum of the cardiomyocyte cell comprises at least one of: the beating frequency, the beating interval between adjacent beats, the beating intensity, the rising time, the relaxation time, the integral area of each beating peak, or combinations thereof.

In embodiments, the beating spectrum of the cardiomyocyte cell can be obtained, for example, at from 35 to 40° C., and preferably at 37° C. under physiological condition, that is, standard cell culture conditions for cardiomyocytes.

In embodiments, the label-free method can further comprise collecting the dynamic mass redistribution (DMR) signal before and after contacting the cardiomyocyte cell with the drug, wherein the RWG biosensor imager collects the beating spectra of the cardiomyocyte cell for a time from, for example, 10 seconds to 1 minute at multiple time points during the assay of from about 30 min to 5 days.

In embodiments, the short period of time can be, for example, 5 min, 1 min, 30 sec, and 10 sec, including intermediate values and ranges. In embodiments, the "long term dynamic mass redistribution" assay can include the real time monitoring of DMR signals of cells in response to stimulation, by tracking the central resonant wavelength of the resonant light over time. "Long term" refers to any time period longer than, for example, about 5 min, 15 min, 30 min, 1 hr, 4 hr, 6 hr, 12 hr, 1 day, 2 day, 5 days, 10 days, and like time intervals, including intermediate values and ranges.

In embodiments, the cardiac effect of a drug molecule can be defined by the abnormality of a beating parameter, compared to that of cardiomyocytes at the resting state (that is, before drug treatment). If the drug treatment results in a beating spectrum having at least one beating interval that is 25% greater than the average interval at the resting state, the drug molecule can be considered to cause irregular beating of cardiomyocyte. Any drug molecule that leads to alterations in beat parameters can be considered to be an effector molecular that interferes with the function of cardiomyocytes. A drug molecule that leads to abnormality of cardiomyocyte beating can be considered to be a cardiotoxic drug molecule.

The present disclosure also provides an alternative label-free method to assess cardiotoxicity of a drug molecule or compound comprising:

culturing a cardiomyocyte cell on the surface of at least one resonant waveguide grating (RWG) biosensor;

illuminating the at least one RWG biosensor using a first swept wavelength interrogation scheme, wherein the first swept wavelength range is at least 5 nm and the swept cycle has a duration of at least 1 second;

determining and averaging the central resonant wavelengths at all pixelated locations of the at least one RWG biosensor using a spatially resolved swept wavelength interrogation resonant waveguide grating imager;

illuminating the at least one RWG biosensor using a second swept wavelength interrogation scheme, wherein the second swept wavelength range is within 3 nm of the average of the central resonant wavelengths at all pixelated locations of the at least one RWG biosensor, and the swept cycle has a duration of less than 0.3 second;

establishing a baseline dynamic mass redistribution (DMR) signal of the at least one RWG biosensor having the cardiomyocyte cell by tracking the central resonant wavelength of the RWG biosensor using the second swept wavelength interrogation scheme;

contacting the cell with a drug molecule;

monitoring with the imager, in real time, the drug molecule induced DMR signal; and comparing the oscillation pattern in the DMR baseline period with the oscillation pattern in the drug molecule induced DMR to determine the drug molecule's cardiotoxicity.

In embodiments, comparing the oscillation patterns of the DMR signal in the baseline period and the drug molecule-induced DMR signal can be, for example, accomplished at a time of from 1 min to 5 days after contacting the cell with the drug molecule, for example, a time of 1 min, 5 min, 10 min, 15 min, 30 min, 1 hr, 4 hr, 8 hr, 1 day, 2 days, 5 days, and like times, including intermediate values and ranges, after contacting the cell with the compound.

The present disclosure also provides a dual function label free method for assessing a cellular response having a low-frequency DMR and a high-frequency beating, the method comprising:

providing at least one resonant waveguide grating (RWG) biosensor and having a cell cultured onto the surface of the at least one biosensor;

illuminating the RWG biosensor using a tunable light source, wherein the tunable light source sweeps the illuminating wavelength within a specific range which covers the resonances of the at least one RWG biosensor;

collecting the spectral images of resonantly reflected light from the at least one RWG biosensor using a high speed optical camera, wherein a series of spectral images are acquired synchronously when the tunable light source sweeps the wavelength through the specific range;

processing the spectral images to:
obtain the central resonant wavelengths at all pixelated locations of the at least one RWG biosensor; and
extract a two-dimensional spatially resolved resonant wavelength image of the at least one RWG biosensor;

monitoring, in real time, the resonant wavelength image of the at least one biosensor using a low-frequency swept wavelength interrogation mode, and the low-frequency is from 0.001 to 1 hertz;

switching the data acquisition from the low-frequency swept wavelength interrogation mode to a high-frequency intensity monitoring mode, wherein the at least one RWG biosensor is illuminated using a second light source having a specific wavelength, and the high-frequency is from 1 to 100 hertz;

monitoring, in real time, the intensity of the light reflected from the at least one RWG biosensor for a time of from 5 seconds to 1 minute to obtain a high-frequency light intensity modulation image;

switching back to the swept wavelength interrogation mode to monitor, in real time, the resonant wavelength image of the at least one RWG biosensor; and processing the resonant wavelength image data to obtain both the high-frequency light intensity modulation spectrum and the low-frequency resonant wavelength dynamic mass redistribution (DMR) signal, wherein the high-frequency light intensity modulation spectrum is used to monitor the high-frequency beating spectrum of the cultured cell, and the low-frequency resonant wavelength DMR signal is used to monitor the cellular response-induced DMR.

In embodiments, the method can further comprise:
contacting the cell with a molecule;
collecting a high-frequency light intensity modulation spectrum at a specific time after the treatment with the molecule, and a low-frequency resonant wavelength DMR signal for the remaining time after the treatment with the molecule;

comparing the high-frequency light intensity modulation spectrum before and after the treatment with the molecule, and the low-frequency resonant wavelength DMR signal before and after the treatment with the molecule, wherein the alteration in the high-frequency light intensity modulation pattern, and the alteration in the low-frequency resonant wavelength DMR signal are indicators of the effect of the molecule on the cultured cell. In embodiments, a tunable light source can sweep the wavelength from a specific range which covers the resonances of the biosensor. In embodiments, the wavelength range can be, for example, from 825 nm to 840 nm. In embodiments, the time to complete a single sweeping can be, for example, 3 seconds, when, for example, a total of 150 frames of images were acquired during the wavelength scan.

In embodiments, the time series of resonant wavelength images of the biosensor can be used to generate a dynamic mass redistribution (DMR) signal. In embodiments, the time series of the intensity images of the light reflected from the biosensor can be used to generate an oscillation pattern of cells without and with the drug treatment. In embodiments, the second illuminating light source can have a specific wavelength from about 100 picometers to 1,500 picometers above the average of the central resonant wavelengths of all pixelated locations of the at least one RWG biosensor, for example, 100 pm, 200 pm, 300 pm, 400 pm, 500 pm, 600 pm, 800 pm, 1000 pm, or 1500 pm, including intermediate values and ranges. In embodiments, the illuminating light source can have a wavelength that is 500 pm above the averaged wavelength of the central resonant wavelengths of all pixelated locations of a biosensor. In embodiments, the second illuminating light source can have a specific wavelength that is from about 100 picometers to about 1,500 picometers below the averaged wavelength of the central resonant wavelengths of all pixelated locations of the at least one RWG biosensor, for example, 100 pm, 200 pm, 300 pm, 400 pm, 500 pm, 600 pm, 800 pm, 1000 pm, or 1500 pm, including intermediate values and ranges.

The present disclosure also provides a label-free method to assess cardiotoxicity of a drug molecule comprising:

culturing a cardiomyocyte cell on the surface of at least one resonant waveguide grating (RWG) biosensor;

in a first mode, illuminating the at least one RWG biosensor using a first swept wavelength interrogation scheme, wherein the first swept wavelength range is at least 5 nm and the swept cycle has a duration of at least 1 second; and monitoring with a spatially resolved swept wavelength interrogation resonant waveguide grating imager, in real time, the central resonant wavelengths at all pixelated locations of the at least one RWG biosensor;

in a second mode, illuminating the at least one RWG biosensor using a second swept wavelength interrogation scheme, wherein the second swept wavelength range is within 3 nm of the average of the central resonant wavelengths at all pixelated locations of the at least one RWG biosensor, and the swept cycle has a duration of less than 0.3 second; and monitoring with the imager, in real time, the central resonant wavelengths at all pixelated locations of the at least one RWG biosensor using a spatially resolved swept wavelength interrogation resonant waveguide grating imager;

in a third mode, illuminating the at least one RWG biosensor using a third light source having a specific wavelength, wherein the third light source has a specific wavelength that is at a specific wavelength above, below or at the average of the central resonant wavelengths of all pixelated locations of the at least one RWG biosensor; and monitoring with the imager, in real time, the intensity of the resonantly reflected light from the at least one RWG biosensor by illuminating with the third light source;

monitoring the cultured cells within the imager using the first mode to obtain the slow dynamic mass redistribution (DMR) response of the cultured cell;

switching the imager from the first mode to the second mode, allowing the imager to monitor the fast DMR response of the cultured cells; and switching the imager from the first or second mode to the third mode, allowing the imager to monitor the high-frequency light intensity modulation signal of the cultured cells, wherein the slow and fast DMR signals and the high-frequency light intensity modulation signal can be used to study the effect of drug molecules on the cultured cell.

The present disclosure also provides a label-free resonant waveguide grating biosensor imager system for measuring beat patterns and dynamic mass redistribution (DMR) signals of cultured cardiomyocytes in the absence and presence of a drug molecule, the system comprising:

a tunable light source that sweeps the illuminating wavelength within a specific range which covers the resonances of at least one RWG biosensor;

a charge-coupled device (CCD) camera that records, for example, in pixelated fashion, the reflected light from the at least one RWG biosensor;

a computer program that calculates the central wavelength of all pixelated locations of the at least one RWG biosensor;

an operating system that allows illuminating the at least one RWG biosensor with three different detection modes, including:

a first mode that illuminates the at least one RWG biosensor using a first swept wavelength interrogation scheme, wherein the first swept wavelength range is at least 5 nm and the swept cycle has a duration of at least 1 second;

a second mode that illuminates the at least one RWG biosensor using a second swept wavelength interrogation scheme, wherein the second swept wavelength range is within 3 nm of the average of the central resonant wavelengths at all pixelated locations of the at least one RWG biosensor, and the swept cycle has a duration of less than 0.3 second; and a third mode that illuminates the at least one RWG biosensor using a third light source having a specific wavelength, wherein the third light source has a specific wavelength that is at a specific wavelength above, below, or at the average of the central resonant wavelengths of all pixelated locations of the at least one RWG biosensor; and a computer and display for extracting and displaying the data obtained using the three different detection modes.

1. Cardiomyocytes

Cardiomyoctye, also termed myocardiocyteal muscle cell, is the cell that comprises cardiac muscle. Cardiac muscle (heart muscle) is a type of involuntary striated muscle found in the walls and histological foundation of the heart, specifically the myocardium. Cardiac muscle is one of three major types of muscle, the others being skeletal and smooth muscle. Cardiomyocytes can contain one, two, or very rarely three or four cell nuclei. Coordinated contractions of cardiac muscle cells in the heart propel blood out of the atria and ventricles to the blood vessels of the left/body/systemic and right/lungs/pulmonary circulatory systems. Cardiac muscle cells, like all tissues in the body, rely on an ample blood supply to deliver oxygen and nutrients and to remove waste products such as carbon dioxide. Cardiac muscle exhibits cross striations formed by alternating segments of thick and thin protein filaments. Like skeletal muscle, the primary structural proteins of cardiac muscle are actin and myosin.

Primary cardiomyocytes are commonly used for in vitro testing of drug-induced cardiotoxicity. These primary cardiomyocytes have the advantage of assembling all cardiac ion channels. While cardiomyocytes provide a system for studying integrated cell physiology, there is significant interspecies variability in the currents contributing to repolarization and in pharmacological sensitivity. Lack of predictive power prevents data derived from animal models from being directly transferred to humans. This is further complicated by a severe shortage of ex vivo human cardiomyocytes for testing purposes. Moreover, adult cardiomyocytes are terminally differentiated with an extremely low proliferative capacity, limiting their use for large screening applications that require substantial volumes of cells. Isolation procedures are time consuming, difficult and costly, and once in culture, ex vivo adult cardiomyocytes rapidly dedifferentiate, hindering phenotypic maintenance in long term culture.

In the recent years, human embryonic or iPS stem cell derived cardiomyocytes have the potential to provide a source of human cardiomyocytes, which may help to overcome problems of species variations. These derived cardiomyocytes may form clusters having some of the characteristics of cardiac tissue, which may also allow assessment of tissue parameters. Furthermore, human stem cells have unrestrictive proliferation and can theoretically serve as an inexhaustible cell source. When propagated in appropriate conditions, hESC are karyotypically and epigenetically stable over many years, providing constancy and reliable provenance, particularly important in drug screening where reproducibility is fundamental. The cardiomyocytes derived from hESC or iPS are very durable under standard in vitro culturing conditions, allowing assessment of both acute effects such as hERG channel inhibition, as well as longer term effects related to extended drug exposure, such as ion channel trafficking. As monolayer preparations or in larger aggregations or clusters, these derived cardiomyocytes exhibit functional synchronization of contraction facilitating studies of cell to cell coupling, signal transduction, and repolarization characteristics. Furthermore, when grouped together as in a cluster or aggregate format, these cardiomyocytes are very robust and tolerate relocation to and from measuring equipment not designed for long term cell culture.

2. Resonant Waveguide Grating Biosensor

An RWG biosensor consists of, for example, a substrate (e.g., glass), a waveguide thin film with an embedded grating structure, and a biological cell layer. The RWG biosensor utilizes the resonant coupling of light into a waveguide by way of a diffraction grating, leading to total internal reflection at the solution-surface interface, which in turn creates an electromagnetic field at the interface. This electromagnetic field is evanescent in nature, such that it decays exponentially from the sensor surface; the distance at which it decays to 1/e of its initial value is known as the penetration depth and is a function of the design of a particular RWG biosensor, but is typically on the order of about 200 nm. This type of biosensor exploits such evanescent waves to characterize, e.g., ligand-induced alterations of a cell layer at or near the sensor surface.

3. Swept Wavelength Resonant Waveguide Grating Imager System

Swept wavelength resonant waveguide grating imager systems have recently been developed (see Ferrie, A. M., et al., Resonant waveguide grating imager for live cell sensing. *Appl. Phys. Lett.* 2010, 97:223704; and Ferrie, A. M., et al., High resolution resonant waveguide grating imager for cell cluster analysis under physiological condition. *Appl. Phys. Lett.* 2012, 100:223701). These RWG imagers have a spatial resolution of, e.g., 12 microns or 80 microns. For the high resolution RWG imager with a spatial resolution of 12 microns, the light beam from a swept tunable light source is directed to focus on, e.g., a 3×4 biosensor array within a 384 well microplate; and a high speed CMOS (complementary metal-oxide semiconductor) digital camera is used to record the escaped and reflected resonant light. The camera has 1400×1024 pixels with a pixel size of 7.4 microns, and the imaging optics has a 1.6× magnification, resulting in an effective spatial resolution of 12 microns. During a single cycle of wavelength sweep from 825 to 840 nm a total of 150 spectral images are acquired every 3 sec, and the spectral image stack is then processed into a sensor resonant wavelength or a DMR image in real time, leading to a temporal resolution of 3 sec. The DMR image is obtained after the starting resonant wavelength, termed basal resonant wavelength at all pixels are normalized to zero. The sweeping in wavelength is stepwise in 100 picometers every 20 milliseconds. Thus, this imager enables a time resolved resonance, wherein the resonant light is coupled into the waveguide at a specific time for a specific location. This leads to improved spatial resolution, although the resonant light can propagate within the waveguide before it leaks out. The imager has a small footprint so it is feasible to be placed inside a bench top cell culture incubator. However, the swept wavelength RWG imager's temporal resolution of about 3 sec prevents its use in detecting a rapid response such as the beating of cardiomyocytes.

4. Dynamic Mass Redistribution Assays

The cellular response to stimulation through a cellular target can be encoded by the spatial and temporal dynamics of downstream signaling networks. For this reason, monitoring the integration of cell signaling in real time can provide physiologically relevant information that is useful in understanding cell biology and physiology. Optical biosensors including resonant waveguide grating (RWG) biosensors, can detect an integrated cellular response related to dynamic redistribution of cellular matter thereby providing a non-invasive means for studying cell signaling. All optical biosensors have in common the ability to measure changes in a local refractive index at or very near the sensor surface. In principle, almost all optical biosensors are applicable to cell sensing, as they can employ an evanescent wave to characterize ligand-induced changes in a cell.

Recently, theoretical and mathematical models have been developed that describe the parameters and nature of optical signals measured in living cells in response to stimulation with ligands. These models, based on a 3-layer waveguide system in combination with known cellular biophysics, link the ligand-induced optical signals to specific cellular processes mediated through a receptor. Because biosensors measure the average response of the cells located at the area illuminated by the incident light, a highly confluent layer of cells can be used to achieve optimal assay results. Due to the large dimension of the cells as compared to the short penetration depth of a biosensor, the sensor configuration is considered as a non-conventional three-layer system: a substrate, a waveguide film with a grating structure, and a cell layer. Thus, a ligand-induced change in effective refractive index (i.e., the detected signal) can be, to first order, directly proportional to the change in refractive index of the bottom portion of the cell layer:

$$\Delta N = S(C) \Delta n_c$$

where $S(C)$ is the sensitivity to the cell layer, and $\Delta n_c$ the ligand-induced change in local refractive index of the cell layer sensed by the biosensor. Because the refractive index of a given volume within a cell is largely determined by the concentrations of bio-molecules such as proteins, $\Delta n_c$ can be assumed to be directly proportional to ligand-induced change in local concentrations of cellular targets or molecular assemblies within the sensing volume. Considering the exponentially decaying nature of the evanescent wave extending away from the sensor surface, the ligand-induced optical signal is governed by:

$$\Delta N = S(C) \alpha d \sum_i \Delta C_i \left[ e^{\frac{-z_i}{\Delta Z_C}} - e^{\frac{-z_{i+1}}{\Delta Z_C}} \right]$$

where $\Delta Z_c$ is the penetration depth into the cell layer, $\alpha$ the specific refraction increment (about 0.18/mL/g for proteins), $z_i$ the distance where the mass redistribution occurs, and d an imaginary thickness of a slice within the cell layer. Here the cell layer is divided into an equal-spaced slice in the vertical direction. The equation above indicates that the ligand-induced optical signal is a sum of mass redistribution occurring at distinct distances away from the sensor surface, each with an unequal contribution to the overall response. Furthermore, the detected signal, in terms of wavelength or angular shifts, is primarily sensitive to mass redistribution occurring perpendicular to the sensor surface. Because of its dynamic nature, it also is referred to as a dynamic mass redistribution (DMR) signal.

Optical biosensor-enabled DMR assays offer a non-invasive means to detect cellular responses in real time. Thus, DMR can be used to characterize a wide range of cellular processes, ranging from cell adhesion, cell proliferation, and cell death. Label-free optical biosensors have gained popularity in studying both biomolecular interactions and cell biology in recent years. Microplate-based resonant waveguide grating (RWG) biosensors have been shown to be able to translate receptor-ligand interactions into dynamic signatures (that is, dynamic mass redistribution) in live cells without labels and/or cell manipulations. The DMR signal is a real time and whole cell phenotypic response, thus offering an unprecedented means to investigate cell biology. However, like almost all microplate reader technologies current label-free systems mostly operate near room temperature without $CO_2$ control, and measure an average response from a population of highly confluent cells.

The present disclosure provides a number of advantages including providing an ability to: 1) have a high frequency measurement method of the beat patterns of cultured cardiomyocytes; 2) simultaneously measure label-free dynamic mass redistribution signals associated with drug-induced cellular responses of cultured cardiomyocytes; 3) measure cellular responses at the single cell and individual cell level; 4) study cardiac biology under physiological conditions; 5) assess cardiotoxicity of drugs including alterations in beat patterns, receptor signaling, and ultimate cell death with a single assay; and 6) measure drug cardiotoxicity with and without synchronized beating of cultured cardiomyocytes.

Materials and Methods:

Chemicals. Gelatin, isoradipine, cisapride monohydrate, E-4031, and astemizole were obtained from Sigma Chemical Co. (St. Louis, Mo.). Isoprotenerol was obtained from Tocris Biosciences Co (St. Louis, Mo.).

Coating of EPIC® resonant waveguide grating (RWG) biosensors. EPIC® 384 well cell culture compatible plates were obtained from Corning, Inc. (Corning, N.Y.). The gelatin-coated EPIC® plates were obtained by incubating the plates with 10 microliter of 20 microgram/mL of freshly prepared gelatin solution in phosphate buffer saline and dried overnight under vacuum. Alternatively or additionally, for example, in experiments with IPS derived cardiomyocytes, the gelatin-coated EPIC® plates were obtained by incubating overnight, uncoated plates with 40 microliters of 0.1% gelatin (Type A) in a solution made with distilled water and autoclaved for 30 minutes to sterilize. The incubated plates were then washed with 40 microliters of sterile water three times immediately before seeding with cardiomyocyte cells. Poly(HEMA-co-MAA-PEO4-VN)-coated EPIC® 384 well biosensor plate was prepared using the following protocols which were previously disclosed in commonly owned and assigned U.S. patent application Ser. No. 13/420,735, filed May 15, 2012. VN is the abbreviation of a vitronectin peptide (KGGPQVTRGDVFTMP). First, a functionalized cell adhesive peptide-copolymer was prepared. Hydroxyethyl methacrylate (HEMA), 60 mg (4.6 mmol), and MAA-PEO4-VN, 1000 mg (0.05 mmol) were added to 75 mL ethanol in an amber flask equipped with a stir bar. Then, 2,2'-azobis-(2-methylbutyronitrile), 90 mg, was added and stirred until completed dissolution. The solution was deoxygenated with an argon purge for 10 min. The sealed flask was then heated for 20 hours at 68° C. under mixing and protected from light. After cooling to room temperature, the poly(HEMA-co-MAA-PEO4-VN) polymer was diluted with 200 mL DMSO and isolated by pouring the crude reaction medium in 1000 mL ethyl acetate. The white solid obtained was washed three times with acetone and vacuum dried. The molecular weight of the poly(HEMA-co-MAA-PEO4-VN) copolymer was determined by size exclusion chromatography (SEC) coupled with a refractive index detector, a light scattering detector, a photodiode array detector, and a viscometer detector. The mobile phase was trifluoroethanol and potassium trifluoroacetate. Average Mn was 58,170, Mw 138,284, and PDI was 2.38. Second, the coating composition was prepared by dissolving 0.5 mg of poly(HEMA-co-MAA-PEO4-VN) copolymer in 10 mL deionized (DI) water. Lastly, the coated EPIC® 384 well cell based assay plate was prepared. To do so, 25 microL of coating composition was dispensed in each well. The plates were then placed into a 50° C. incubator for 30 minutes to allow copolymer adsorption. After cooling to room temperature, the plates were rinsed one time by means of a gentle tap water flow. Then a 1% SDS solution, 30 microL, was added to each well and incubated for about 30 min. Then the plates were rinsed four times with deionized water. Finally the plates were dried by spinning (plate placed upside-down) at 800 rpm for one minute Immobilized peptide density was determined by a bicinchoninic acid (BCA) assay using a BCA protein quantification kit from Uptima. Standards were prepared using the VN peptide in PBS. Absorbance was read on a BIOTEK® Synergy 4. BCA showed that the amount of immobilized peptide was about 15 pmol/mm$^2$.

Resonant waveguide grating biosensor imager system. The optical reader instrument is based on swept wavelength imaging technology.

First Mode The resonant waveguide grating biosensor is illuminated at a normal incidence angle by a collimated LED (light emitting diode) beam, which passes through a tunable optical filter with a pass band width of 1 nm. The illuminated sensor area was imaged to a high speed CMOS (complementary metal-oxide-semiconductor) camera. Spectral images were acquired synchronously when the tunable filter sweeps through a wavelength range which covers the resonances of the biosensors. The image stack contains sensor spectra in all the pixels, where resonance wavelengths are extracted in a 2D image. Normally in each acquisition, the wavelength sweep is from 825 nm to 840 nm, or 820 nm to 835 nm for a duration of 3 seconds, and 150 frames of images were acquired during the wavelength scan. For typical long-term DMR assays, the update rate was from 15 seconds to minutes, with multiple scans averaged into a single data point. This is a first mode of operation for obtaining DMR responses, which responses are slower than 3 seconds; this mode is referred to as the slow resonant wavelength imaging DMR mode or slow DMR mode (sDMR). The three modes of operation are summarized in Table 1.

Second Mode To detect fast dynamic mass redistribution such as that caused by beating of cardiomyocytes, the data acquisition rate needs to be increased correspondingly. To accurately sample the beating signal, the measurement update rate needs to be faster than the Nyquist frequency of about 4 Hz, which is four times the beat frequency of about 1 Hz. Thus, a resonant waveguide grating imager was established that was capable of supporting a second mode of operation. This second mode of operation operates to have the swept wavelength imaging update rate near or faster than the Nyquist frequency. The second mode is referred to fast resonant wavelength imaging DMR mode or fast DMR mode (fDMR). This can be achieved by employing a high speed camera and a fast tunable light source. The second mode can also use a conventional camera having a speed of about 60 frames per second. The update rate can be increased to about 4 Hz if, for example, only 12 frames are taken in one scan, and the tuning range is closely matched to the central resonant wavelength range of the sensor resonances. Since the sensor spectrum is sparsely sampled, the resonance measurement noise may not be as optimal as in the first mode, but the measurement speed is gained while maintaining a quantifiable resonance wavelength of the sensor. When the measurement update rate is slightly less or slower than the Nyquist frequency, the measurement is no longer accurate due to aliasing. However, frequency and amplitude of the beat can still provide qualitative information.

TABLE 1

| Modes of Operation | | | |
| --- | --- | --- | --- |
| Mode | Update rate | Data Point(s) Characterization | Operation |
| First (slow resonant | 3 sec or 3 sec multiples | multiple scans averaged into a | Swept wavelength range of 15 nm |

TABLE 1-continued

Modes of Operation

| Mode | Update rate | Data Point(s) Characterization | Operation |
| --- | --- | --- | --- |
| wavelength imaging DMR)(sDMR) | | single data point | |
| Second (fast DMR) (fDMR) | near the Nyquist frequency | Single scan per data point | Swept wavelength range of 3 nm |
| Third (Intensity imaging) | >10 Hz | Single or multiple scan per data point | Intensity (power) monitoring at a fixed wavelength |

Third Mode In a third mode of operation, the update rate can be further increased far beyond the Nyquist frequency by setting the light source wavelength to the waist points of the resonance spectrum, where a change of resonance wavelength is translated into the intensity modulation of the reflected beam. The third mode is referred to as the intensity (or power) imaging mode. For example, if the interrogated sensor spectral width is 3 nm, linearity is maintained for about ±0.5 nm, and modulation can be obtained over a larger range. The linear dynamic range can be further increased by widening the sensor resonance or the width of the tunable filter, the tradeoff being a reduced slope of wavelength shift versus intensity change. Monitoring the optical power can further reference out the drift of the light source intensity. The update rate in this detection scheme is limited only by the frame rate of the camera, which can be, for example, from 30 Hz to 1000 Hz depending on the speed of the digital camera selected. The camera preferably can have a deep full well capacity to reduce the shot noise. A number of variations can be achieved within this mode of operation. For example, the light source can switch between two wavelengths on both sides of the center resonance in a push-pull operation, where common mode noise from the light source can be cancelled. The light source can also switch among multiple wavelengths if the wavelength variation of the sensors is larger than the operating range.

The above fast measurement methods in the second mode and the third mode can be combined with the first mode operation to provide DMR information in multiple time scales. For cardiomyocyte assays in particular, simultaneously capturing the conventional slow DMR kinetics and the fast DMR kinetics associated with beating in a single cell or single cell cluster resolution offers a unique advantage compared to existing technologies. The beat frequency of cardiomyocytes is typically 1 Hz, and the Nyquist frequency is 4 Hz. In this example, conventional DMR images are acquired at an update rate of 12 seconds. fDMR images are measured at a 10 Hz update rate, with each data point being the average of, for example, six frames. The update rate can be still faster if necessary, the tradeoff being the increased size of data files.

Culture of iPS derived cardiomyocytes. iCELL® Cardiomyocytes were obtained from Cellular Dynamics International. These iPS derived cardiomyocytes are highly purified human cardiomyocytes derived from iPS cells. The cells express monomeric red fluorescent protein (mRFP) and blasticidin resistance, both of which are under the control of the alpha-myosin heavy chain (Myh6) promoter that allows simultaneous cardiomyocyte purification and identification. iCELL® Cardiomyocytes are a mixture of spontaneously electrically active atrial, nodal, and ventricular-like myocytes that possess typical electrophysiological characteristics and exhibit expected electrophysiological and biochemical responses upon exposure to exogenous agents. Because cardiac tissue shows species-specific protein expression patterns, use of terminally differentiated human cardiomyocytes, rather than other surrogate models (e.g., cadaveric or animal cells, and transformed immortalized cells lines), for drug discovery and toxicity testing is expected to generate results that more accurately predict the relevant in vivo human response. The use of iCELL® Cardiomyocytes can save time, resources, and compound. iCELL® Cardiomyocytes are differentiated from human pluripotent stem cells, maintained in vitro, and thus provide an easily accessible and physiologically relevant model system for assessing compound effects on human cardiac cellular electrophysiology. iCELL® Cardiomyocytes exhibit standard biochemical and electrophysiological characteristics of normal human heart cells, that form electrically connected syncytial layers that beat in synchrony, and have a demonstrated utility in numerous biochemical assays and arrhythmia testing. The cryopreserved suspensions of dissociated cells as received were directly plated into EPIC® plates using the iCELL® Cardiomyocytes Plating Medium, and maintained in iCELL® Cardiomyocytes Maintenance Media according to the protocols recommended by the supplier. The beating of cardiomyocytes was detected 4 days after culture and became synchronized afterwards. iCELL® Cardiomyocytes remain viable in culture for up to two weeks, thus enabling assessment of both short-term and longer-term toxicity testing. All measurements were taken at 37° C. in a functional cell culture incubator.

Results and Discussion

The RWG imager was first used to obtain basal resonant wavelength images of a 3×4 biosensor array within a 384 well EPIC® biosensor plate coated with gelatin. The images were obtained 4 days after culture of iPS derived cardiomyocytes. The cardiomyocytes formed a monolayer on the surfaces of the biosensors. FIG. 1 shows a false colored basal resonant wavelength image of the biosensor arrays. Individual cells can be resolved due to its high spatial resolution (12 microns). The high resolution RWG imager was based on our recently developed whole plate imager with a spatial resolution of 80 micron (A. M. Ferrie, et al., *Appl Phys Lett*, 97, 223704 (2010)). Instead of illuminating the whole plate, the light beam from a swept tunable light source was directed to focus on a 3×4 biosensor array within a 384 well microplate. A high speed CMOS (complementary metal-oxide semiconductor) digital camera was used to record the reflected resonant light. The reflected resonant light is due to escaping or leaking out of the resonant light from the waveguide thin film. The camera has 1400×1024 pixels with a pixel size of 7.4 micrometers, and the imaging optics has a 1.6× magnification, resulting in an effective spatial resolution of 12 micrometers. During a single cycle of a wavelength sweep from 825 to 840 nm a total of 150 spectral images were acquired every 3 sec, and the spectral image stack was processed into sensor resonant wavelength or DMR image in real time, leading to a temporal resolution of 3 sec. The DMR image was obtained after the starting resonant wavelength, termed basal resonant wavelength, at all locations were normalized to zero. The wavelength sweeping was stepwise in 100 picometer (pm) every 20 milliseconds. The resonant wavelengths within a sensor was found to be within a specific range, depending on multiple factors including, for example, differences in sensor configuration, cell confluency, degree of cell adhesion, cellular response, or combinations thereof. This imager provides a way to introduce a time resolved resonance, wherein the resonant light is coupled into the waveguide at a specific time for a specific location. This leads to improved spatial resolution, although the resonant light can propagate within the waveguide before it leaks out. Furthermore, the imager has a small footprint so the imager can be placed inside a bench top cell culture incubator.

Next, the impact of two different surface coatings, gelatin-coated and a vitronectin peptide coated EPIC® biosensor microplates, for the cell growth, cell beating and synchronized beating of cultured cardiomyocytes, was tested. The results showed that both surfaces led to comparable cell morphology, cell viability, and time to start beating and time to reach synchronized beating of iPS derived cardiomyocytes.

Figure 2:
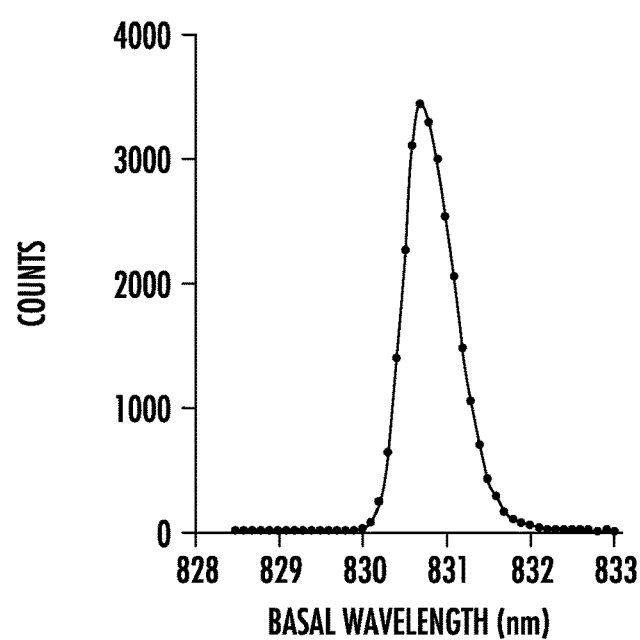
FIG. 2 is a graph that shows the distribution of the basal resonant wavelengths at each pixel of a RWG biosensor having cultured human iPS-derived cardiomyocyte cells.

Thereafter, the distribution of basal resonant wavelengths at all pixelated positions of a single biosensor within the array as shown in FIG. 1 was analyzed. The distribution shows a single peak centered around 830.7 nm having a peak width of about 1.5 nm as shown in FIG. 2, suggesting that the basal resonant wavelength after the formation of the cell monolayer is quite uniform. FIG. 2 is a graph that shows the distribution of the basal resonant wavelengths at each pixel of a RWG biosensor having cultured human iPS-derived cardiomyocyte cells. The number of pixel whose basal resonant wavelength is within a specific range (i.e., bin size, typically 100 pm) defines the total counts.

Figure 3:
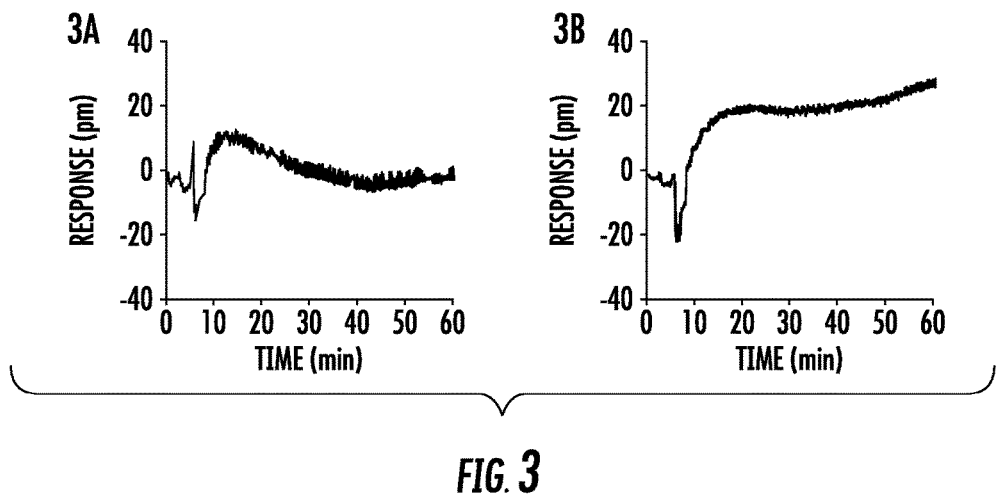
FIGS. 3A and 3B are graphs that respectively show the dynamic mass redistribution signals of cultured human iPS-derived cardiomyocytes induced by the assay buffer, that is, the negative control (FIG. 3A), and 160 nM isoproterenol (FIG. 3B).

Next, the DMR signal of cultured cardiomyocytes in response to stimulation with the beta2-adrenergic receptor agonist compound, isoprotenerol, was examined. The results showed that compared to the negative control, which the assay vehicle solution led to a small DMR signal, the isoprotenerol at 160 nM resulted in a more sustained DMR signal in the cardiomyocytes at from 35 to 40° C., and preferably at 37° C. under physiological conditions (FIG. 3). Interestingly, after stimulation by contacting with isoprotenerol, the oscillation pattern of the DMR signal became smaller but with higher frequency, compared to the baseline and the DMR induced by the assay buffer, suggesting that the isoprotenerol caused increased beating but with smaller amplitude of the cultured cardiomyocytes.

Figure 4:
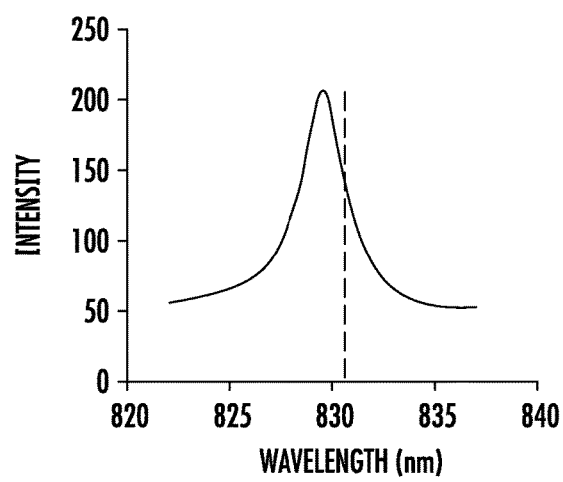
FIG. 4 is a graph that shows the averaged resonant peak of a RWG biosensor having cultured human iPS-derived cardiomyocyte cells.

Next, the averaged resonant peak of the biosensor was analyzed. The averaged resonant peak was obtained after averaging all resonant peaks at each pixel of the biosensor. As shown in FIG. 4, the resonant peak is relatively wide. The dotted line in FIG. 4 shows the wavelength used to establish the intensity monitoring operation scheme, i.e., the third operational mode of the biosensor imager system, and the operating wavelength selected for monitoring the beat pattern of the cultured cardiomyocytes. The use of a light having a wavelength that is higher than the averaged central resonant wavelength leads to a beat spectrum of cultured cardiomyocytes that consists of a series of minimal peaks (FIG. 7). Conversely, the use of a light with a wavelength that is lower than the averaged central resonant wavelength leads to a beat pattern that consists of a series of positive peaks. This is demonstrated by the intensity images obtained and shown in FIGS. 5 and 6.

Figure 5:
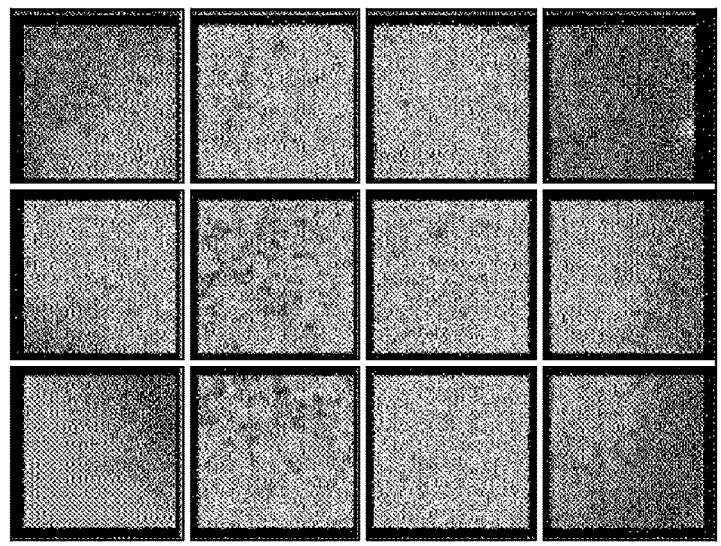
FIG. 5 is a false colored resonant light intensity image of a 3×4 array of RWG biosensors in an EPIC® 384 well microplate.

FIG. 5 shows a false colored intensity image of a 3×4 biosensor array within an VN peptide coated 384 well EPIC® microplate having a monolayer of cultured cardiomyocytes. This image was obtained by monitoring the resonant light intensity after the light used for illumination of the biosensor was set to a value above the central wavelength, that is the resonant wavelength, of the biosensors, as indicated in FIG. 4.

Figure 6:
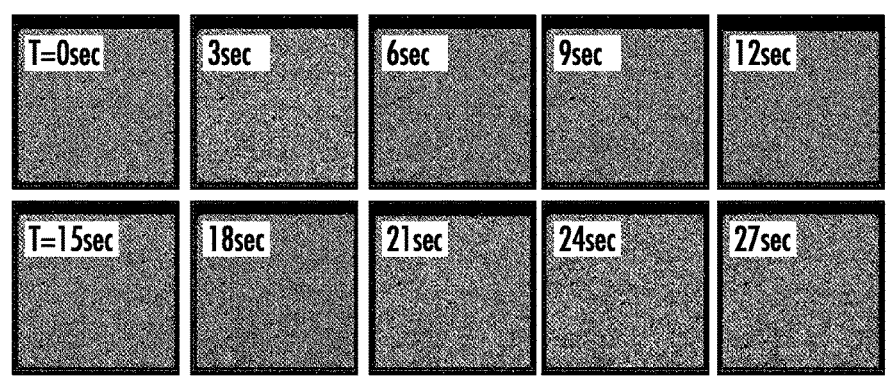
FIG. 6 shows a time series from left to right, from 0 to 27 seconds, of false colored resonant light intensity images of a RWG biosensor having cultured human iPS derived cardiomyocyte cells under resting state.
Figure 7:
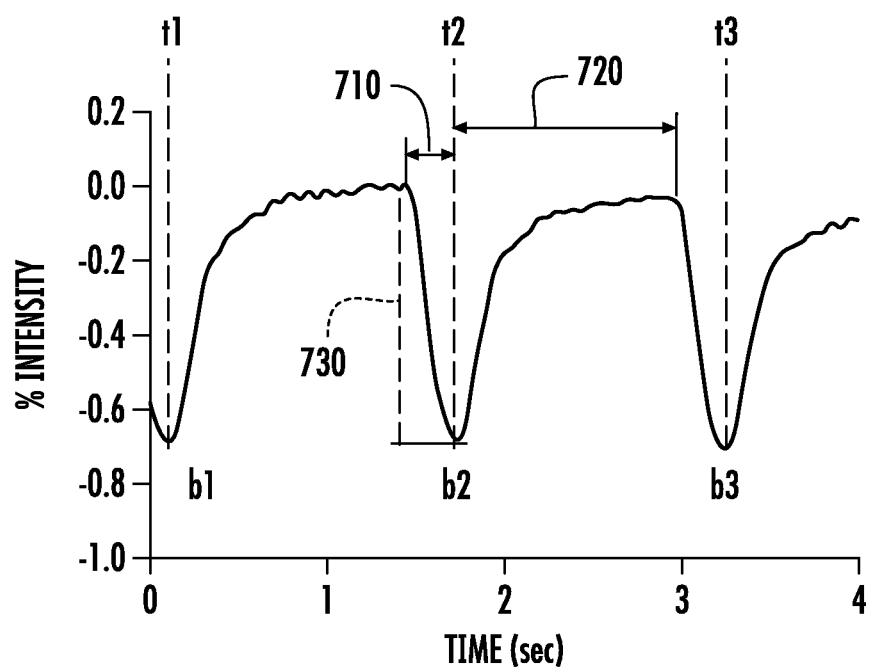
FIG. 7 is a graph that shows a typical beat pattern for beats of cultured human iPS derived cardiomyocytes and key parameters including: rise time, relaxation time, and % intensity or beat intensity that define the beat pattern.

FIG. 6 shows a false colored intensity map of a single biosensor having cultured cardiomyocytes after stimulation with 1 micromolar epinephrine, an agonist for endogenous adrenergic receptors in cardiomyocytes. The cardiomyocytes were cultured for 4 days on the biosensor surface and had not established synchronized beating. Results showed that under this non-synchronized beating condition the imager was capable of detecting the beating of individual single cardiomyocytes, as evidenced by the increased intensity (i.e., the reddish or darker shade dots) at specific time points, i.e., 3 sec, 21 sec, 24 sec, and 27 sec. FIG. 6 shows a time series from left to right, from 0 to 27 seconds, of false colored resonant light intensity images of a RWG biosensor having cultured human iPS derived cardiomyocyte cells under resting state. The change in the intensity of the resonant light at each pixel is an indicator of beating of a single cardiomyocyte cell. An increase in light intensity (red color) at a given pixel indicates the beating of the cell at the respective location. The non-uniform beating observed, as indicated by the non-uniform changes in resonant light intensity image, suggests that the cultured iPS derived cardiomyocyte cells have not achieved a synchronized beating state. The synchronized beating state reflects a state wherein the cardiomyocyte cells beat at the same time, resulting in a characteristic beating pattern of the resonant light intensity.

Next, the beat patterns of cultured cardiomyocytes were monitored after the cells had established a synchronized beating. Results showed that under the synchronized beating condition obtained after 7 days culture, the cardiomyocytes exhibited a regular and reproducible beating with a beat rate of about 55 times per minute, and a beat intensity of −0.6. The beat pattern was obtained using an illumination light whose wavelength is 400 pm higher than the averaged central resonant wavelength. FIG. 7 is a graph that shows a typical beat pattern for beats (b1 to b2, and b2 to b3) of cultured human iPS derived cardiomyocytes and key parameters including: rise time (710), relaxation time (720), and % intensity (730) or beat intensity, that define the beat pattern. As shown in FIG. 7, kinetic parameters can be extracted from analyzing the beating behavior of cardiomyocytes, so it is possible to determine the potential cardiotoxicity induced by a compound, such as drug molecule or drug candidate. The kinetic parameters include: 1) the beat time; 2) the interval between two adjacent beats; 3) the rise time of each beat; 4) the relaxation time of each beat; and 5) the beat intensity and area per peak. Statistical analysis can then be performed to determine the irregularity of any beat spectrum of cultured cardiomyocytes.

Figure 8:
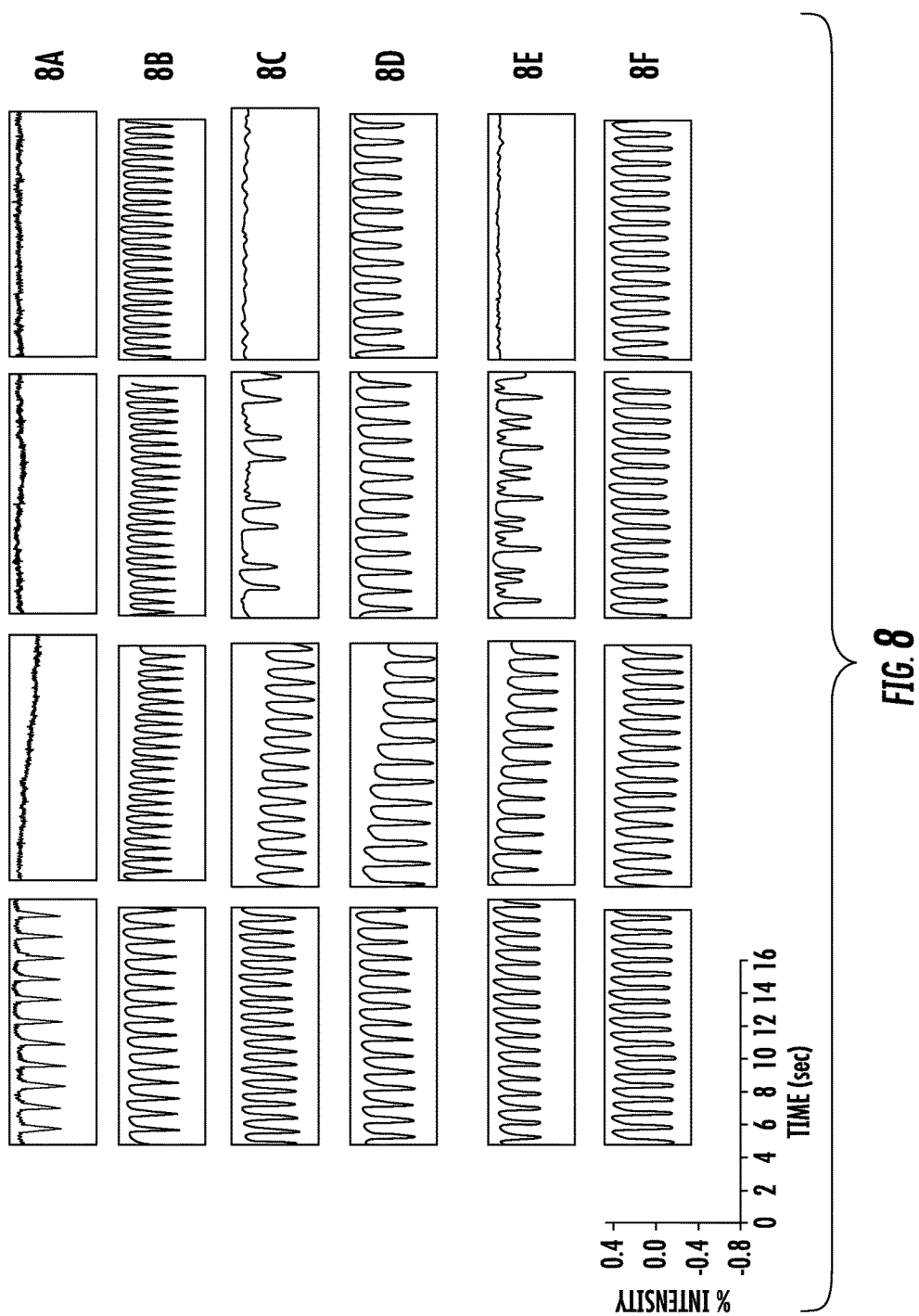
FIG. 8 provides an exemplary series of graphs (A through F) that show time dependent alteration in beat pattern of cultured human iPS-derived cardiomyocytes before contact (the baseline; left column) and measurements over time (see % beat intensity versus time inset) after contact or stimulation with specific drug molecules.

Next, the impact of a series of drug molecules on the beat spectrum of cardiomyocytes was examined. For each drug, the baseline beat spectrum of cardiomyocytes was first obtained and used as a reference to determine the impact of each compound or drug molecule. Next, multiple beat spectra were obtained, each at a specific time after the drug stimulation (e.g., 1 min, 5 min, 15 min), so that both short term and long term toxicity of the drug molecules could be examined FIG. 8 provides a series of graphs (A through F) that show time dependent alteration in beat pattern of cultured human iPS-derived cardiomyocytes before contact (the baseline; left column) and measurements over time (see % beat intensity versus time inset) after contact or stimulation with specific drug molecules (col. 2=1 min, col. 3=5 min, col. 4=15 min post-stimulation) for: 10 micromolar Isradipine (Row A); 10 micromolar (−)-Isoproterenol (Row B); 10 micromolar cisapride monohydrate (Row C); 10 micromolar E-4031 (Row D); 10 micromolar astemizole (Row E); and 0.025% DMSO (Row F). As shown in FIG. 8, the results indicated that isradipine at 10 micromolar largely suppressed the beating of cultured cardiomyocytes, and isradipine suppression was rapid and occurred as soon as the cells were exposed to the drug. Conversely, isoprotenerol increased the beat frequency but suppressed its beat amplitude or strength; and the isoproterenol induced alteration in beat patterns lasted for some time. Cisapride time-dependently altered the beat pattern of cultured cardiomyocytes, and ultimately stopped the beating. E-4031 and astemizole also led to an altered beat pattern, while the negative control (the vehicle solution containing 0.025% DMSO) had little effects on the beat pattern.

Figure 9:
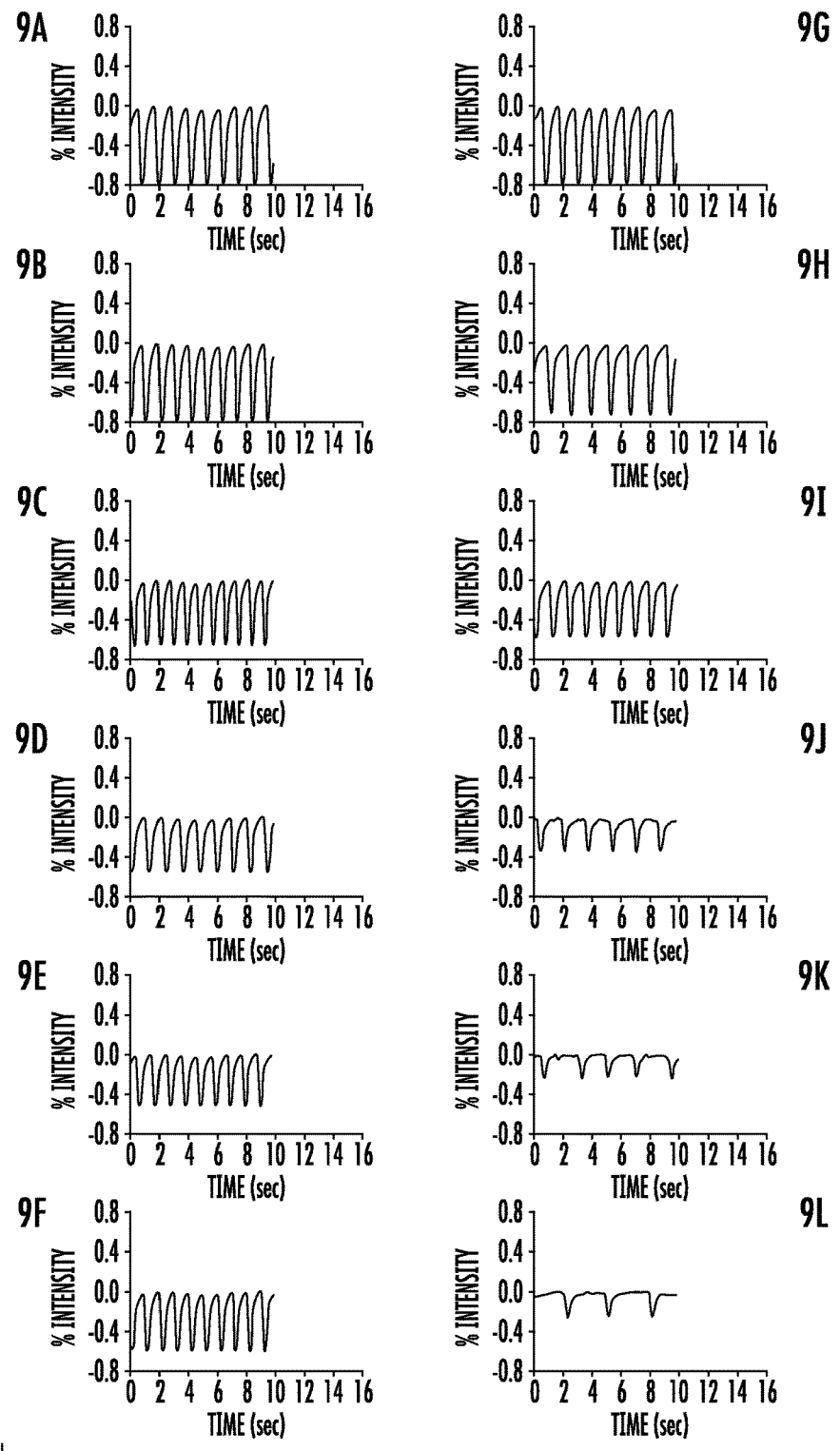
FIG. 9 provides a series of graphs (a through l) that show the impact of cisapride at different doses on the beating of cultured cardiomyocytes: the beating of cardiomyocytes before stimulation; and the beating of corresponding cardiomyocytes 15 min after being treated with cisapride at different doses.
Figure 10:
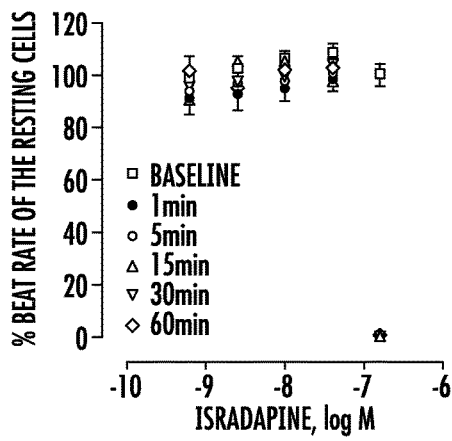
FIGS. 10A and 10B show graphs of the time and dose-dependent alteration of the beat rate of cultured cardiomyocytes induced by israpadine. The results of two independent duplicate experiments are shown (left and right).
Figure 10:
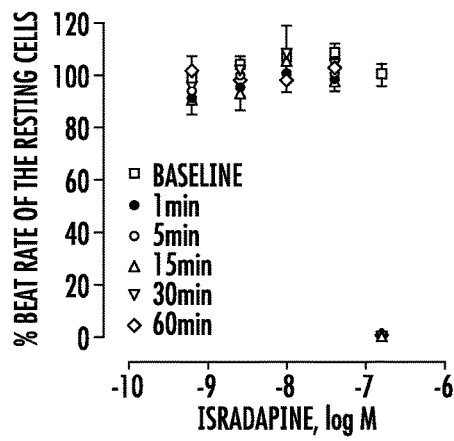
Figure 11:
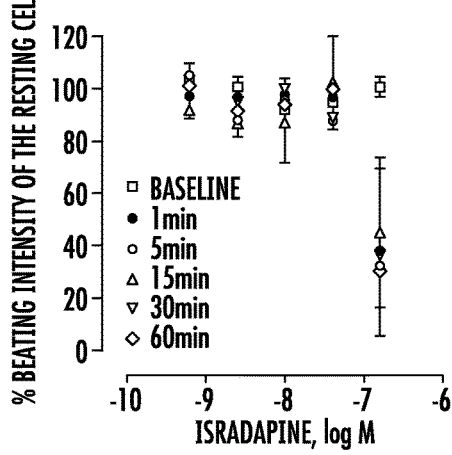
FIGS. 11A and 11B show graphs of the time and dose-dependent alteration of the beat intensity of cultured cardiomyocytes induced by israpadine. The results of two independent duplicate experiments are shown (left and right).
Figure 11:
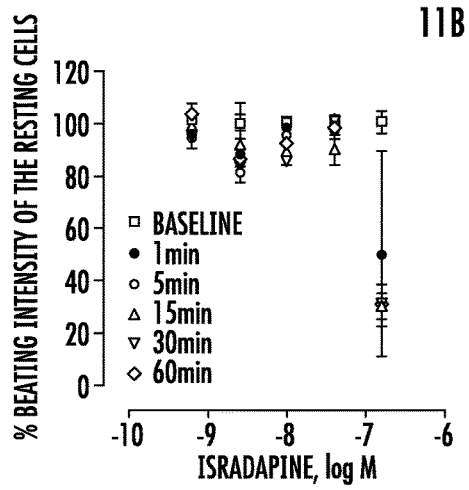

Lastly, the dose dependent effect of both cisapride and israpadine were determined. FIG. 9 provides a series of graphs (a through l) that show the impact of cisapride at different doses on the beating of cultured cardiomyocytes: the beating of cardiomyocytes before stimulation (i.e., without any treatment or control) (left column: a to f); and the beating of corresponding cardiomyocytes 15 min after treated with cisapride at different doses (right column: g to l); graph (g) has 0 micromolar cisapride (that is, the assay buffer only); graph (h) has 0.16 micromolar cisapride; graph (i) has 0.62 micromolar cisapride; graph (j) has 2.5 micromolar cisapride; graph (k) has 10 micromolar cisapride; graph (l) has 40 micromolar cisapride. The results demonstrated in FIG. 9 showed that cisapride dose-dependently decreased both the beat rate and amplitude, with an $IC_{50}$ of about 160 nM Similarly, israpadine also dose-dependently blocked the beating of cultured cardiomyocytes, with an $IC_{50}$ of about 100 nM as discussed for FIGS. 10 and 11. Specifically, FIGS. 10A and 10B show graphs of the time and dose-dependent alteration of the beat rate of cultured cardiomyocytes induced by israpadine. The results of two independent duplicate experiments are shown (left and right). FIGS. 11A and 11B show graphs of the time and dose-dependent alteration of the beat intensity of cultured cardiomyocytes induced by israpadine. The results of two independent duplicate experiments are shown (left and right). The results suggest that the high frequency imager is capable of detecting the cardiomyocyte beating and drug molecule induced cardiotoxicity.

The disclosure has been described with reference to various specific embodiments and techniques. However, many variations and modifications are possible while remaining within the scope of the disclosure.

The invention claimed is:

1. A label-free method to detect a drug-induced cardiac effect comprising:
culturing a cardiomyocyte cell on the surface of at least one resonant waveguide grating (RWG) biosensor;
illuminating the at least one RWG biosensor using a swept wavelength interrogation resonant waveguide grating biosensor imager with a first light source having a first wavelength;
collecting the resonant spectra at all pixelated locations of the at least one biosensor and determining the average of the central resonant wavelengths of all pixelated locations of the at least one RWG biosensor with the swept wavelength interrogation resonant waveguide grating biosensor imager;
illuminating the at least one RWG biosensor using a second light source having a second wavelength and monitoring with the imager, in real time, the intensity of the resonantly reflected light to obtain a beating spectrum of the cardiomyocyte cell in a resting state;
contacting the resting state cardiomyocyte cell with a drug molecule;
illuminating the drug-contacted cardiomyocyte cell on the surface of the at least one RWG biosensor using the second light source and monitoring with the imager, in real time, the intensity of the resonantly reflected light to obtain a beating spectrum of the drug-contacted cardiomyocyte cell; and
extracting and comparing at least one beating parameter of the beating spectrum of the resting state cardiomyocyte cell and the beating spectrum of the drug-contacted cardiomyocyte cell, wherein the drug-induced alteration of the at least one beating parameter is an indicator of the cardiac effect of the drug.

2. The method of claim 1, wherein the cardiomyocyte cell comprises at least one of a human primary cardiomyocyte, an animal primary cardiomyocyte, a human embryonic stem cell derived cardiomyocyte, a human induced pluripotent stem cell (iPS cell) derived cardiomyocyte, an animal induced pluripotent stem cell (iPS cell) derived cardiomyocyte, or a combination thereof.

3. The method of claim 1, wherein the surface of the resonant waveguide grating biosensor contains a coating having an extracellular matrix protein, a cardiomyocyte compatible synthetic material, or a combination thereof.

4. The method of claim 3, wherein the coating comprises at least one of fibronectin, matrigel, collagen I, collagen IV, gelatin, poly(HEMA-co-MAA-PEO4-vitronectin) peptide conjugate, or a combination thereof.

5. The method of claim 1, wherein the resonant waveguide grating biosensor imager has a spatial resolution from 3 microns to 500 microns.

6. The method of claim 1, wherein the wavelength of the second light source is at least one of:
from 100 to 1,500 picometers above the average of the central resonant wavelengths of all pixelated locations of the at least one RWG biosensor;
from 100 to 1,500 picometers below the average of the central resonant wavelengths of all pixelated locations of the at least one RWG biosensor; or
the average of the central resonant wavelengths of all pixelated locations of the at least one RWG biosensor.

7. The method of claim 1, wherein the cardiomyocyte cell is a plurality of cells, and culturing the plurality of cells is accomplished at from 35 to 40° C. for a time of from 5 days to 2 weeks until synchronized beating is achieved.

8. The method of claim 1, wherein the drug is at least one of: a marketed drug molecule; a preclinical drug candidate molecule; an exploratory drug candidate molecule; or a combination thereof.

9. The method of claim 1, wherein the beating spectrum of the cardiomyocyte cell has a temporal resolution of from 0.01 second to 1 second.

10. The method of claim 1, wherein the beating spectrum of the drug-contacted cardiomyocyte cell is obtained in from about 1 minute to 5 days after exposure to the drug molecule.

11. The method of claim 1, wherein the at least one beating parameter of the beating spectrum of the cardiomyocyte cell comprises at least one of: the beating frequency, the beating interval between adjacent beats, the beating intensity, the rising time, the relaxation time, the integral area of each beating peak, or combinations thereof.

12. The method of claim 1, further comprising collecting the dynamic mass redistribution (DMR) signal before and after contacting the cardiomyocyte cell with the drug, wherein the RWG biosensor imager collects the beating spectra of the cardiomyocyte cell for a time from 10 seconds to 1 minute at multiple time points during the assay of from about 30 min to 5 days, and the RWG biosensor imager collects the DMR signal throughout the remaining time of the assay.

* * * * *

UNITED STATES PATENT AND TRADEMARK OFFICE
CERTIFICATE OF CORRECTION

PATENT NO. : 10,203,320 B2
APPLICATION NO. : 14/437275
DATED : February 12, 2019
INVENTOR(S) : Oberon Denaci Deichmann et al.

Page 1 of 1

It is certified that error appears in the above-identified patent and that said Letters Patent is hereby corrected as shown below:

On the Title Page

Column 2, item (56), other publications, Line 19, delete "Lettets," and insert -- Letters, --, therefor.

Signed and Sealed this
Twentieth Day of August, 2019

Andrei Iancu
*Director of the United States Patent and Trademark Office*